United States Patent [19]

Stanton et al.

[11] Patent Number: 4,803,170

[45] Date of Patent: Feb. 7, 1989

[54] COMPETITIVE IMMUNOASSAY METHOD, DEVICE AND TEST KIT

[75] Inventors: Thomas H. Stanton, Seattle; James A. Clagett, Everett; Deborah C. Schindele; George E. Renzoni, both of Bothell; Niels H. Andersen; Kent E. Opheim, both of Seattle, all of Wash.

[73] Assignee: Ultra Diagnostics Corporation, Seattle, Wash.

[21] Appl. No.: 946,475

[22] Filed: Dec. 24, 1986

Related U.S. Application Data

[63] Continuation-in-part of Ser. No. 732,445, May 9, 1985, Pat. No. 4,746,631.

[51] Int. Cl.[4] .................... G01N 33/53; G01N 33/543
[52] U.S. Cl. .................... 436/518; 436/514; 436/807; 436/808; 436/809; 422/61; 422/56
[58] Field of Search .................. 435/7, 805, 810; 436/518, 532, 535, 514, 807, 808, 809, 810, 819, 820; 422/56, 57, 58, 61

[56] References Cited

U.S. PATENT DOCUMENTS

| | | | |
|---|---|---|---|
| 3,715,192 | 2/1973 | Wenz et al. | 422/56 |
| 4,146,365 | 3/1979 | Kay et al. | 422/57 |
| 4,235,869 | 11/1980 | Schwarzberg | 436/512 |
| 4,272,478 | 6/1981 | Vihko | 422/57 |
| 4,289,747 | 9/1981 | Chu | 424/1 |
| 4,330,299 | 5/1982 | Cerami | 23/230 B |
| 4,425,438 | 1/1984 | Bauman et al. | 436/527 |
| 4,446,232 | 5/1984 | Liotta | 435/7 |
| 4,472,498 | 9/1984 | Masuda et al. | 435/805 |
| 4,478,942 | 10/1984 | Katsuyama et al. | 436/66 |
| 4,506,009 | 3/1985 | Lenhoff et al. | 435/810 |

Primary Examiner—Sam Rosen
Assistant Examiner—Janelle Graeter
Attorney, Agent, or Firm—Christensen, O'Connor, Johnson & Kindness

[57] ABSTRACT

An immunoassay device including one or more reaction chambers, each adapted to receive and retain a volume of test fluid in fluid communication with nonoverlapping first, second, and third reagent-bearing surfaces. To the first surface is reversibly bound an analyte conjugate: analyte component conjugated to one or more components, termed ligand/marker, that serve ligand and marker functions as described herein. Analyte binding partner is immobilized on the second surface, and ligand/marker binding partner is immobilized on the third surface. The reaction chamber is preferably configured to receive and direct the test fluid sequentially past the first second, and third reagent surfaces. In use, analyte conjugate solubilized from the first surface completes with any analyte in the test fluid for analyte binding partner sites on the second surface. Excess analyte conjugate becomes sequestered on the third surface, where the marker activity is read to indicate analyte presence and concentration in the test fluid. A test kit includes the immunoassay device in combination with comparative test results.

30 Claims, 4 Drawing Sheets

COMPETITIVE IMMUNOASSAY METHOD, DEVICE AND TEST KIT

This is a continuation-in-part of application Ser. No. 732,445, filed May 9, 1985, now U.S. Pat. No. 4,746,631.

TECHNICAL FIELD

This invention relates to immunoassays and more particularly to heterogeneous immunoassays in which analyte in test fluid either displaces or competes with a labeled moiety.

BACKGROUND OF THE INVENTION

Various heterogeneous immunoassays for the detection and quantification of analyte molecules in a liquid sample are known, and several employ the displacement of a labeled moiety from an insoluble support.

In this regard, U.S. Pat. No. 4,330,299 is of interest for disclosing a method for measuring the level of glucose in animal body fluids which comprises contacting a portion of a given body fluid with a glucose indicator comprising a reversible complex of a carbohydrate component, a binding macromolecular component, and an indicator element bound to one of the components. The sample of body fluid is maintained in contact with the glucose indicator for a period of time sufficient to permit the glucose present to displace the carbohydrate component in the reversible complex, whereby the indicator element is released to signify the presence of glucose. This assay suffers from the disadvantage that its applicability is restricted to glucose and other sugars.

U.S. Pat. No. 4,425,438 discloses an assay method and flowthrough test device in which test substance may displace an analytical reagent, which can be the test substance chemical labeled with a detectable group and with a group capable of binding specifically to an analytical absorbant, from a primary absorbant. A column is provided with two zones, a primary absorbant zone and an analytical absorbant zone, through which the assay fluid, admixed with a predetermined quantity of analytical reagent, is sequentially passed. Any analytical reagent not bound by the primary absorbant substance becomes bound to the analytical absorbant substance. The presence of analytical reagent bound to the analytical absorbant substance is then determined. A principal disadvantage of this assay is that the specific amounts of primary absorbant in the primary absorbant zone and of analytical reagent mixed with the assay fluid must be carefully balanced to ensure that no analytical reagent will pass through the beads if no test substance is present, and, at the same time, at least some analytical reagent will pass through the beads if test substance is present in the assay fluid.

U.S. Pat. No. 4,434,236 discloses an immunoassay wherein labeled antibody having greater affinity for analyte in the fluid sample than for immobilized analyte-analog is displaced from the solid phase. A principal disadvantage of this assay is that the fluid sample containing displaced labeled antibody must be analyzed by means, such as by spectrophotometer or fluorometer, that do not lend themselves to home or field use. Another disadvantage is that labeled divalent antibodies cannot be accurately employed in this assay.

Immunoassays based upon competitive binding between a targeted analyte and a labeled analyte reagent, for available analyte-specific binding sites on an insoluble support, have also been described.

While perhaps advantageous for certain applications, few or none of the prior art devices and methods provide a single-step, self-contained test device that can be conveniently used by a nontechnical user for on-site testing. It would also be advantageous to provide an integrated device that can be conveniently manufactured and used to detect and quantify the presence of several different analytes in a single application, preferably for real-time testing.

SUMMARY OF THE INVENTION

This invention provides a single step, self-contained test device for detecting and quantifying analyte molecules in a fluid sample. No auxiliary reactants other than a test fluid need be supplied or added to this test device, which can be conveniently used by the lay public in the home or field without auxiliary instrumentation. Moreover, an integrated test device is provided that can be conveniently custom-manufactured and used to detect and quantify several different analytes in a simple application.

The disclosed test device includes one or more reaction chambers of this invention. Two embodiments of the subject reaction chambers are disclosed, one based on displacement binding and the other on competitive binding. In either embodiment, each reaction chamber is adapted to receive and retain a volume of test fluid in fluid communication with nonoverlapping first and second reaction surfaces. Considering first the displacement binding embodiment, to the first reaction surface is immobilized analyte binding partner that is in turn saturated with analyte conjugate: analyte component conjugated to one or more components, collectively termed ligand/marker, that serve ligand and marker functions as described herein. The analyte conjugate has a higher dissociation constant with reference to the immobilized analyte binding partner than does the analyte to be assayed. To the second reaction surface is immobilized ligand/marker binding partner.

In the practice of this invention, a test fluid sample is introduced into the disclosed reaction chamber and retained therein to permit two reactions to occur. In a first reaction between analyte and analyte binding partner at the first reaction surface, analyte proportionately displaces analyte conjugate into the test fluid sample. In a second reaction the displaced analyte conjugate becomes sequestered at the second reaction surface by bonding with immobilized ligand/marker binding partner. Thereafter the marker activity of sequestered analyte analog is measured, the measured activity being a function of the analyte concentration that is referable to standards and controls.

In the competitive binding embodiment, the subject reaction chamber houses three reagent-bearing surfaces. Here the analyte conjugate is reversibly bound in solubilizable form to a first reagent surface. A second reagent surface conforms to the first reaction surface described above except that only the analyte binding partner is bound thereto. The third reagent surface (like the above-described second reaction surface) has the ligand/marker binding partner immobilized thereon. The reaction chamber is preferably configured to receive and direct the test fluid sequentially past the first, second, and third reagent surfaces, some or all of which can be microporous membranes. In use, analyte conjugate is solubilized from the first surface and competes with any analyte in the test fluid for analyte binding partner binding sites on the second surface. Excess analyte conjugate becomes sequestered on the third surface, where its marker activity can be read as an indication of analyte presence and concentration in the test fluid.

Also provided are test kits that include the disclosed test device(s) in combination with comparative test results that associate sequestered ligand/marker activity with specific concentrations of analyte in test fluid.

DESCRIPTION OF THE PREFERRED EMBODIMENT

The disclosed test device includes one or more reaction chambers for detecting the presence and concentration of analyte in a test fluid. Two embodiments of the subject reaction chambers are disclosed, one based on displacement binding and the other on competitive binding.

Figure 1:
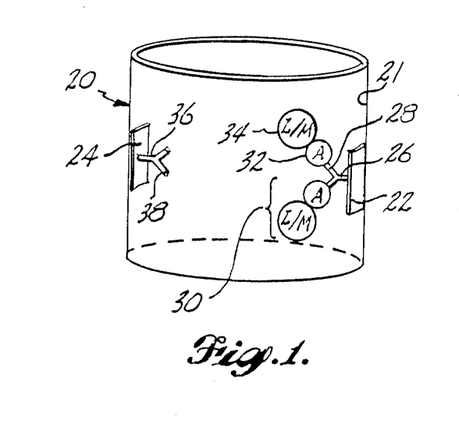
FIG. 1 is a schematic diagram of an immunoassay reaction chamber of this invention, wherein an analyte binding partner having analyte-specific binding sites that are saturated with analyte conjugate (analyte component conjugated with ligand/marker component) is immobilized on a first reaction surface, and wherein a ligand/marker binding partner is immobilized on a second reaction surface.

Considering first the displacement binding system, FIG. 1 shows a reaction chamber 20 designed to receive and retain a volume of test fluid and provided with containment walls 21 and with first and second reaction surfaces 22, 24. The reaction surfaces 22, 24 are disposed in nonoverlapping and preferably noncontiguous arrangement within the reaction chamber 20 such that the first reaction surface 22 is in fluid communication with the second reaction surface 24 after a predetermined volume of test fluid is introduced into the reaction chamber 20. To the first reaction surface 22 a multiplicity, on the order of millions, of analyte binding partners 26 are immobilized such that in the preferred embodiment analyte-specific binding sites 28 on the immobilized analyte binding partners 26 are potentially available in log excess over the expected concentration of analyte in the predetermined volume of test fluid. The available analyte-specific binding sites 28 on the immobilized analyte binding partners 26 are saturated with analyte conjugate 30, which in the simplest embodiment consists of an analyte molecule 32 conjugated with a ligand/marker molecule 34. The analyte binding partner 26 is selected such that its analyte-specific binding sites 28 have a higher affinity for free analyte in the test fluid than for the particular analyte conjugate 30; that is, under the assay conditions the analyte conjugate 30 has a higher dissociation constant with reference to the analyte binding partner 26 than does the analyte in the test fluid. To the second reaction surface 24 a multiplicity of ligand/marker binding partners 36 are immobilized such that ligand/marker-specific binding sites 38 on the immobilized ligand/marker binding partners 36 are available in log excess over the expected concentration of analyte in the predetermined volume of test fluid.

Figure 2:
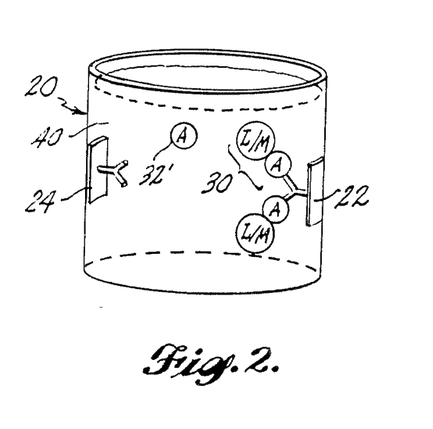
FIG. 2 is identical to FIG. 1 except that a test fluid sample containing analyte has been introduced into the reaction chamber.
Figure 3:
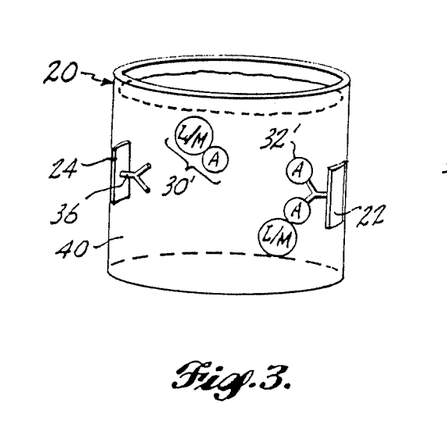
FIG. 3 is identical to FIG. 2 except that analyte in the retained test fluid sample has displaced analyte analog from analyte-specific binding site at the first reaction surface, and the displaced analyte analog has diffused or been mixed into the test fluid sample.
Figure 4:
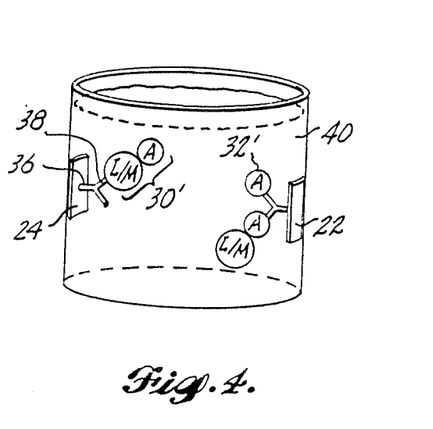
FIG. 4 is identical to FIG. 3 except that the displaced analyte conjugate has contacted and bound to ligand/marker binding partner at the second reaction surface.
Figure 5:
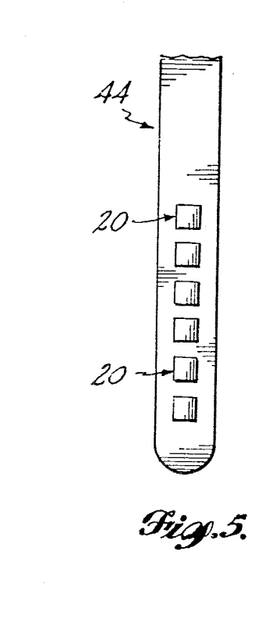
FIG. 5 is a plan view of a dipstick having a plurality of displacement-binding reaction chambers of this invention.

Referring now to FIGS. 1, 2, 3, and 4, a method is provided for detecting the presence and concentration of an analyte in a test fluid. A reaction chamber 20 is provided in accordance with the foregoing discussion referring to FIG. 1. Referring to FIG. 2, a volume of test fluid 40 containing (or suspected of containing) analyte molecules 32' is introduced into the reaction chamber 20 so that at least parts of the first and second reaction surfaces 22, 24 are covered by the test fluid sample 40. For stoichiometric quantification of analyte 32' concentration a predetermined volume of test fluid 40 should be introduced into the reaction chamber 20 and, furthermore, the first and second reaction surfaces 22, 24 should be thereby completely submersed. Referring to FIGS. 2, 3, and 4, the test fluid sample 40 is retained within the reaction chamber 20 for an incubation period that can be on the order of thirty minutes, depending upon ambient temperature. During the incubation period two reactions occur within the fluid-filled reaction chamber 20. At the first reaction surface 22 analyte 32' will displace analyte conjugate 30 from analyte binding partner 26, which displacement reaction proceeds by virtue of the higher affinity of the analyte-specific binding sites 28 for analyte 32' than for analyte conjugate 30. Any displaced analyte conjugate 30' diffuses through the test fluid sample 40, which diffusion process can be enhanced by stirring the test fluid sample 40, and upon contacting the second reaction surface 24 the displaced analyte conjugate 30' binds to ligand-/marker binding partner 36 via a bond between ligand-/marker component 34 and ligand/marker-specific binding site 38. Subsequent to the incubation period the marker activity of the ligand/marker 34 on the second reaction surface 24 is measured, that activity being a function of the concentration of analyte 32' in the test fluid and referable to standards and controls.

In order to simplify this discussion, analyte 32' is considered unless otherwise stated to be an immunogenic molecule such as an antigen or hapten, and analyte binding partner 26 is considered to be an antibody having analyte 32'-specific binding sites 28, as this is the preferred embodiment. However, in the practice of this invention, analyte 32' can be any molecule for which an analyte binding partner 26 exists or can be raised or synthesized. Thus, it is also contemplated that in the practice of this invention analyte 32' can be an antibody and analyte binding partner 26 can be an antigen or hapten, in which case both the analyte and the analyte component of the analyte conjugate would have binding sites (not shown) that are specifically reactive with the immunogenic analyte binding partner immobilized on the first reaction surface 22.

Test fluid sample 40 can be any aqueous source of analyte 32'; for example, physiological fluids such as anti-coagulated blood, plasma, urine, tissue extract, or saliva, in which case the analyte 32' can be any endogenous or exogenous molecule, such as a hormone or a therapeutic or abused drug and their metabolites. Test fluid 40 must be aqueous or largely so, containing only small amounts of organic solvents so that analyte binding partner 26 and analyte conjugate 30 will not spontaneously dissociate in the test fluid sample 40. In this regard, the analyte 32' must also be available in aqueous solution for binding with analyte binding partner 26. Thus, to detect serum protein-bound hormones such as cortisol, detergent can be added to the test fluid sample 40 in order to release the hormone analyte 32' from the protein carrier and thereby make it fully available to an analyte binding partner 26 having cortisol-specific binding sites 38. Such detergents and other agents, where applicable, can be placed on the containment walls 21, e.g., by evaporation or impregnation, prior to packaging the reaction chamber 20, in order to maintain the simplicity of the disclosed assay protocol.

Reaction chamber 20 is configured to receive a test fluid sample 40 and retain the same (including any displaced analyte conjugate 30') throughout the incubation period. For stoichiometrical determinations of analyte 32' concentration, reaction chambers 20 of uniform volume should be provided. The containment walls 21 (other than the reaction surfaces 22, 24) that contain the test fluid sample 40 within the reaction chamber 20 can be made of any insoluble material, e.g., plastic, nylon, polypropylene, polyvinylchloride, or polyvinylcarbonate, that does not react with either analyte 32' or displaced analyte conjugate 30'. Reaction chambers 20 of this invention can take the form of test tubes, microtiter wells, or self-contained dipsticks as described below.

First reaction surface 22 and second reaction surface 24 are each composed of a binding substrate, which can be a molecular film, having the capacity to bind reactants via covalent or strong ionic bonds such that analyte binding partner 26 and ligand/marker binding partner 36 can be irreversibly immobilized on the first and second reaction surfaces 22, 24, respectively. Suitable binding substrates for this purpose include derivatized celluloses such as nitrocellulose, bromacetyl cellulose, cyanogen bromide activated cellulose, and also derivatized nylon, derivatized plastics, and other activated polymers.

Analyte binding partner 26 is preferably a monoclonal antibody having at least one binding site 28 that is specifically reactive to analyte 32' and to analyte component 32 and that in addition has a higher affinity for analyte 32' than for analyte conjugate 30. Analyte binding partner 26 can be a divalent antibody or an antibody polymer (or polymerized Fab fragments) having a plurality of analyte-specific binding sites 28. However, it is contemplated that steric hindrance between the available analyte-specific binding sites 28 should be minimized for stoichiometrical quantification purposes, in which case a monovalent antibody or Fab fragment is the preferred analyte binding partner 26.

Analyte binding partner 26 can be covalently bonded to first reaction surface 22 by conventional techniques; for example, by conventional reactions involving carbonyl groups, carboxyl groups, the $\epsilon$-amino acid groups of lysine, or the SH groups of cysteine, by strong ionic interactions, and by specific interaction with protein A. In this displacement-binding embodiment, a multiplicity of analyte binding partners 26 are bound to the first reaction surface 22 so that analyte-specific binding sites 28 are thereafter available for binding with analyte 32' or analyte component 32 in log excess over the expected concentration of analyte 32' in the test fluid sample 40. To this end, through the use of heterobifunctional chemical compounds and through other chemical reactions known in the art, analyte binding partner 26 can be immobilized on first reaction surface 22 in specific orientation in order to make analyte-specific binding site 28 available to analyte component 32 of analyte conjugate 30 and to analyte 32' in test fluid sample 40. Moreover, the accessibility with regard to steric hindrance of available analyte-specific binding sites 28 can be enhanced by selectively distributing analyte binding partner 26 on the first reaction surface 22. Optimal density of particular analyte binding partners 26 can be achieved by selective chemical activation of the first reaction surface 22 or by using immunoaffinity membranes 22 that are commercially available, e.g., BIODYNE immunoaffinity membrane (PALL, Biodyne Division, Glen Cove, N.Y.).

Analyte conjugate 30 is a conjugated molecule: analyte component 32 bonded to ligand/marker 34. Ligand/marker 34 is a molecule or molecules or conjugated molecule that perform(s) two functions: Ligand-/marker 34 acts as a ligand to provide specific binding of displaced analyte conjugate 30' to ligand/marker binding partner 36 at the second reaction surface 24. Ligand/marker 34 also acts as a marker that can be detected by conventional techniques such as enzymatic color development. For certain applications ligand-/marker 34 may also perform a third function by acting as a macromolecular carrier in order to ensure the retention of displaced analyte conjugate 30' within the reaction chamber 20.

The aforesaid functions can be performed by ligand/markers 34 that consist of either a single molecule, or a conjugate of a ligand component bonded to a marker component, or a conjugate of a carrier component bonded to both a ligand component and a marker component. Alternatively, a ligand component and marker component can be individually conjugated at separate sites to the analyte component 32 to make analyte conjugate 30. For example, the fluorescent phycobiliprotein molecule can act as a convenient ligand/marker 34 that advantageously combines the aforesaid ligand, marker, and macromolecular carrier functions in a single molecule. As another example, ligand/marker 34 can be horseradish peroxidase (HPO) conjugated with a ligand such as biotin, in which case the HPO, having a molecular weight of about 40,000, functions both as a marker component and as a macromolecular carrier.

Suitable ligand components include: biotin, bovine serum albumin (BSA), synthetic peptides, phycobiliproteins, and $\beta$-galactosidase, all of which have readily available ligand/marker binding partners 36 as described below.

Suitable marker components include: enzymes such as HPO, $\beta$-galactosidase, and alkaline phosphatase; chromophores or organic dyes such as phthalocyanines, particularly copper, silicon, and aluminum phthalocyanines; fluorophores such as fluorescein, phycobiliprotein, or rhodamine; phosphorescent markers such as monometalloporphyrins, particularly ytterbium porphyrin and platinum porphyrin and their derivatives, particularly the tetraphenylporphyrins and tetracarboxytetraphenylporphyrins; coenzymes such as FAD; chemiluminescent materials such as luciferin; enzyme inhibitors such as phosphonates; and radionuclides. If the marker component is an enzyme useful for colorimetric assay, the reaction product should be insoluble so that the marker activity will be sequestered at the second reaction surface 24. Peroxidase substrates fulfill this requirement. Chemiluminescence, due to the extraordinary sensitivity of the enhanced signal, is preferred for detecting analyte 32' such as hormones at very low concentrations.

Suitable macromolecular carrier components include BSA and other proteins of greater than, e.g., 10,000, molecular weight. Smaller synthetic peptides can also be employed as carrier components to focus the analyte component 32 and the ligand/marker component(s) 34 in specific orientation on the analyte conjugate 30.

In embodiments in which analyte 32' is an immunogenic molecule, the analyte component 32 of the analyte conjugate 30 can have the same molecular structure as the analyte 32' to be assayed or can be a metabolic derivative or a synthesized or raised analog thereof. For example, analyte component 32 can be an anti-idiotype antibody to analyte-specific binding site 28. In embodiments wherein analyte 32' is an antibody, the analyte component 32 can be the same or a different antibody. In all embodiments the analyte component 32 must specifically bind to analyte binding partner 26 and, for the displacement-binding embodiments, analyte component 32 when conjugated to ligand/marker 34 must have a higher dissociation constant than analyte 32' with reference to analyte binding partner 26.

Monoclonal antibodies can be raised using standard techniques of in vivo or in vitro immunizations. Selection of hybridoma clones producing antibodies with the requisite affinities can be performed by equilibrium dialysis or by determining of relative dissociation constants through a modification of the Farr technique, both as described in Chapters 15 and 16 *Handbook of Experimental Immunology; Vol. 1: Immunochemistry*, Weir (ed.), Blackwell Scientific Publications, G.B., 1973, which are hereby incorporated by reference. Fab fragments of monoclonal antibodies can be prepared as described in *J. Immunol.* 131:2895-2902, 1983. Heterobifunctional compounds are disclosed in *Biochem. J.* 173:723-737, 1978.

For optimal stoichiometry as many ligand components as possible should be substituted onto analyte conjugate 30 while maintaining the activity of the marker component; also, analyte conjugates 30 should each bear a uniform number of marker components.

To make analyte conjugate 30, ligand/marker 34 can be conjugated to analyte component 32 using strong ionic or covalent bonding, by diazotization, by water soluble carbodiimides, by utilizing available carboxyl groups and amino groups, and by heterobifunctional compounds and other chemical linkages known in the art.

The available analyte-specific binding sites 28 on the first reaction surface 22 are saturated with analyte analog 30 in a separate preparative manufacturing step by incubation for at least one hour at room temperature, followed by removal of excess, unbound analyte conjugates 30 by washing with physiologic salt solution.

Ligand/marker binding partner 36 can be a monoclonal or polyclonal antibody having specific affinity for ligand/marker 34 component (but not for analyte 32 component) of analyte conjugate 30. For example, if BSA serves as the ligand component in ligand/marker 34, then anti-BSA can serve as the ligand/marker binding partner 36. As another example, if biotin serves as the ligand component in ligand/marker 34, then ligand/marker binding partner 36 can be insolubilized avidin. Other representative but nonlimiting examples of ligand/marker binding partners 36 include second partners of activated heterobifunctional substituted ligand/markers 34. Ligand/marker binding partner 36 is irreversibly immobilized on second reaction surface 24 as described above so that ligand/marker-specific binding sites 38 are available for binding to ligand/marker 34 in log excess of the expected concentration of analyte 32' (and, porportionally, of displaced analyte conjugate 30') in test fluid sample 40.

Referring now to FIGS. 5 through 14, an improved dipstick 44, 44' can be provided with one or more reaction chambers 20, 20' of this invention.

Figure 6:
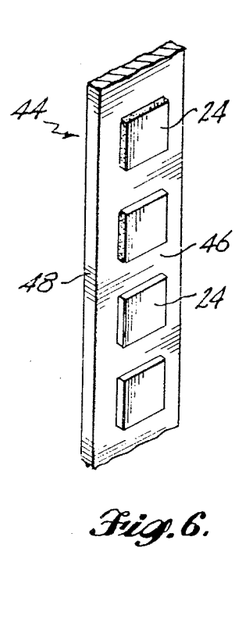
FIG. 6 is an oblique view showing a spaced series of second reaction surfaces on the test surface of the displacement-binding dipstick.
Figure 7:
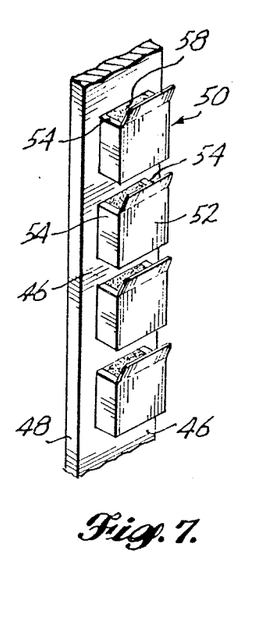
FIG. 7 is a view similar to FIG. 6 except that a series of reaction chamber housings are cooperatively mounted on the test surface to span and cover the second reaction surfaces.
Figure 8:
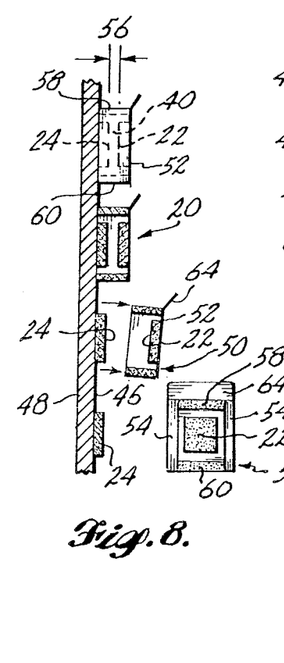
FIG. 8 is a section of the device of FIG. 7 showing juxtaposed first and second reaction surfaces within the reaction chambers and also indicating the detachable mounting of the reaction chamber housing and wicks.

Referring first to FIGS. 6 through 8, a representative embodiment of a displacement binding dipstick 44 is shown. In dipstick 44, a plurality of second reaction surfaces 24 are disposed in spaced array along a test surface 46 of an insoluble support 48. Each second reaction surface 24 is completely covered by an insoluble, impermeable reaction chamber housing 50 that can have the form of a U-shaped channel with a web 52 and two opposing flanges 54. A first reaction surface 22 is disposed on the web 52 between the flanges 54. The flanges 54 are positioned on and detachably mounted to the test surface 46 so that the housing 50 spans the second reaction surface 24 and juxtaposes the two reaction surfaces 22, 24. The flanges 54 are of a height selected so that a minimum diffusion distance 56, no more than about 1.0 mm and preferably on the order of 0.1 mm, separates the first and second reaction surfaces 22, 24.

Upper and lower membranes 58, 60 cooperate with the open ends of the housing 50 and with the adjacent test surface 46 to complete the containment walls of a reaction chamber 20 having a test fluid volume capacity on the order of 10 to 50 μl. The flanges 54 of housing 50 are detachably mounted on the test surface 46, for example by an insoluble adhesive (not shown) having low shear strength. Membranes 58, 60 are typically made of materials having very low shear strength and so can be cooperatively attached to the web 52, flanges 54, and adjacent test surface 46 by any insoluble cement.

The upper and lower membranes 58, 60 function primarily to facilitate the capillary migration of test fluid into the reaction chamber 20. To this end the membranes 58, 60 can each be an open meshwork of very hydrophilic material such as cellulose that, once the dipstick 44 is immersed in test fluid, acts as a wick to draw a test fluid sample into the reaction chamber 20. For certain applications it may be desirable to exclude macromolecules such as plasma proteins from the reaction chamber 20, in which case the membranes 58, 60 can be made of a hydrophilic meshwork having a molecular size exclusion limit. For example, polysulfone membranes and cellulosic polymers may be used to exclude macromolecules of 10,000 molecular weight or larger, and also to retain within the reaction chamber 20 displaced analyte conjugate of the specified size. In another embodiment, the lower membrane 60 can be any of the aforementioned hydrophilic wicks, but the upper membrane 58 can be made of a hydrophobic meshwork or porous membrane that acts as a one-way valve to facilitate release of entrapped air as the reaction chamber 20 fills with test fluid. If avidin is used as ligand/marker binding partner 36, then the outside surfaces of membranes 58, 60 can be loaded with insolubilized avidin in order to remove any biotin intrinsic to the test fluid sample.

A tab 64 can be provided as an integral part of each reaction chamber housing 50, on the side of the web 52 opposite the first reaction surface 22, to facilitate detachment of the housing 50 from the test surface 46. Tab 64 also can be applied to a web 52' that integrates a series of reactor chamber housings (see FIG. 9).

In operation, the dipstick 44 is immersed in a test fluid, such as urine, until the reaction chambers 20 are completely filled with a test fluid sample by capillary migration of test fluid through the upper and/or lower membranes 58, 60. The dipstick 44 is then removed from the test fluid and laid on a flat surface, test surface 46 upward, for the duration of the incubation period. During the incubation period surface tension resulting from the hydrophilic nature of the membrane(s) 58, 60 retains the test fluid sample within the reaction chamber 20. After the incubation period has elapsed the tab 64 is pulled to detach the reaction chamber housing 50 from the test surface 46 and thereby expose the second reaction surface 24 for visual or instrumental determination of sequestered ligand/marker activity.

Figure 9:
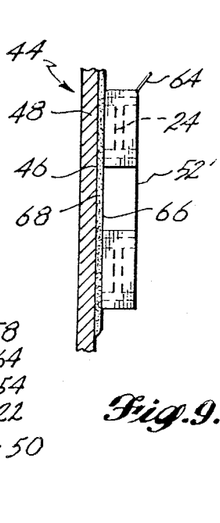
FIG. 9 is a view similar to FIG. 8 but showing an embodiment wherein substrate is releasably sequestered on the insoluble support.

Referring to FIG. 9, if the marker activity on the second reaction surface 24 is to be measured colorimetrically by employment of an enzyme marker component such as HPR in ligand/marker 34, then the appropriate substrate can be incorporated into the dipstick 44. For example, substrate 68 can be sandwiched between the test surface 46 and an insoluble, frangible membrane 66, such as Mylar, adjacent the second reaction surface 24 and stored there until the incubation period is over. Then the membrane 66 can be crushed to release substrate 68 onto the second reaction surface 24 for local color development due to reaction with any ligand/enzyme marker bound thereon. Substrate 68 can take the form of substrate-saturated membranes as well. Thus the present invention supplies a self-contained test device 44 to which no auxiliary reactants other than test fluid 40 need be added. Such a test device 44 permits a simple, one-dip assay that has obvious advantages for home and field use.

The test device 44 can be provided in kit form in combination with comparative test results, e.g., a color chart (not shown), that associate the enzyme marker activity with specific concentrations of analyte in test fluid.

Dipsticks 44 of this invention can be conveniently manufactured as well as conveniently used to simultaneously detect and quantify the presence of different analytes in a test fluid. For example, dipstick 44 can be supplied with a plurality of second reaction surfaces 24 each having the same ligand/marker binding partner, e.g., avidin, immobilized thereon. In contrast, the corresponding first reaction surfaces 22 can bear different analyte binding partners to which different analyte conjugates are reversibly bound. However, if the same ligand/marker, e.g., biotin/HPR, is employed throughout, so that the various analyte conjugates differ only with respect to their analyte components, then the same substrate can be used to develop marker activity on each second reaction surface. Moreover, the user can refer to the same color chart to determine the specific concentrations of the different analytes as functions of the observed marker activities on the various second reaction surfaces.

To optimize stoichiometric quantification the following conditions should be met: analyte-specific binding sites must significantly exceed the number of analyte molecules in the test fluid sample; the dissociation constant of analyte binding partner with respect to analyte analog must be greater than the dissociation constant with respect to analyte; displaced analyte analog must bind essentially irreversibly to ligand/marker binding partner; the time period for developing marker activity on the second reaction surface must be routinely adjusted to render color intensity, fluorescence intensity, or other detectable parameters in direct relation to the quantity of analyte present in the test fluid sample; and ligand-analog displacement from analyte binding partner must be associated with analyte binding only. These conditions are met by the reaction chambers of this invention.

Referring now to FIGS. 10 through 14, a competitive binding dipstick 44' is provided with one or more reaction chambers 20'. As described below, reaction chamber 20' is configured to receive and direct a predetermined volume (e.g., 10 to 100 μl) of test fluid (e.g., urine or plasma) containing the targeted analyte (e.g., a drug metabolite or allergen) sequentially past and preferably through the first and second reaction surfaces 22, 24.

Figures 10, 11, 12:
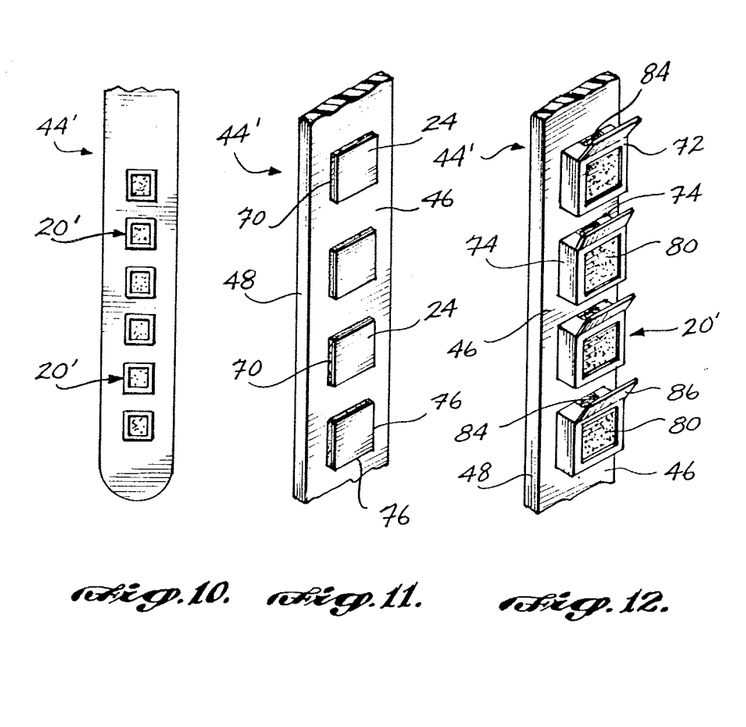
FIG. 10 is a plan view of a dipstick having a plurality of competitive-binding reaction chambers of this invention.
FIG. 11 is an oblique view showing a spaced series of second reaction surfaces on the test surface of the competitive-binding dipstick.
FIG. 12 is a view similar to FIG. 11 showing a series of reaction chamber housings cooperatively mounted on the test surface to span and cover the second reaction surfaces.
Figures 13, 14:
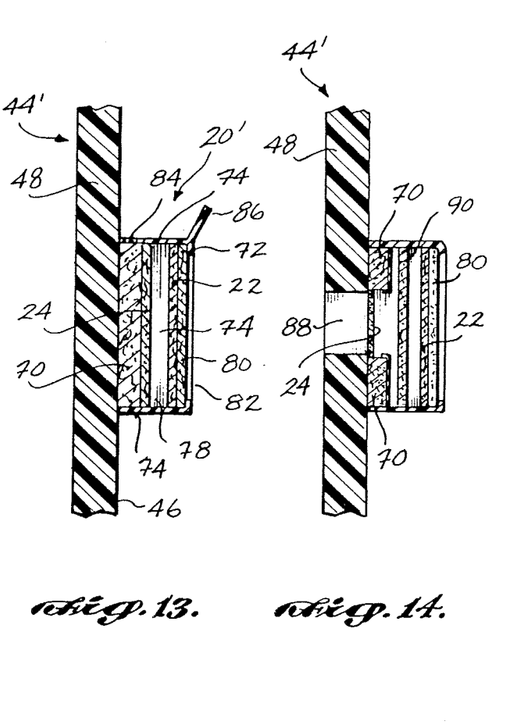
FIG. 13 is a section of a reaction chamber from FIGS. 10 and 12, showing juxtaposed first and second reaction surfaces within the detachable housing and also the relative positions of the wick and analyte analog-bearing membrane, with the arrow indicating the direction of test fluid flow sequentially through these porous membranes.
FIG. 14 shows in section view another embodiment of the competitive-binding chamber, here fitted with a viewing port for convenient readout of marker sequestered on the second reaction surface.

In the representative embodiment shown in FIGS. 11 through 13, a plurality of second reaction surfaces 24 are disposed in spaced array along a test surface 46 of an insoluble support 48. Here, each second reaction surface 24 is preferably composed of a porous binding substrate, and a hydrophylic membrane 70 of substantially the same dimensions as 24 is preferably sandwiched between the porous reaction surface 24 and the test surface 46. Each second reaction surface 24 and underlying membrane 70 are enveloped by an insoluble, impermeable reaction chamber housing 72. Housing 72 has sidewalls 74 that are positioned on and detachably mounted to the test surface 46. The sidewalls 74 should also contiguously border the lateral margins 76 of at least the second reaction surface 24 and thereby house the underlying membrane 70 in a separate compartment, so that fluid communication with membrane 70 can only be established through porous second reaction surface 24.

A first reaction surface 22 is disposed in the distal (meaning away from surface 46) end of housing 72, and separated from second reaction surface 24 by a cavity 78 of predetermined volume. A reagent membrane 80 is positioned in the housing 72 distal to the first reaction surface 22. Distal to membrane 80, the housing 72 has an aperture 82 that opens to the environment. First reaction surface 22 and reagent membrane 80 are, like second reaction surface 24, porous to the passage of test fluid, including dissolved or entrained analyte (32'). Sidewalls 74 similarly envelope the lateral margins 76 of first reaction surface 22 and reagent membrane 80. Thus, the distal end of housing 72 is configured so that fluid communication with cavity 78 can only be established by the passage of test fluid through aperture 82 and then sequentially through reagent membrane 80 and first reaction surface 22.

As discussed above, analyte binding partner (26) and ligand/marker binding partner (36) are bound to the first and second reaction surfaces 22, 24, respectively. For use in competitive binding reaction chambers 20', the association constants of binding partner 26, with reference to the free analyte 32' and the analyte component 32 of analyte conjugate 30, can be identical. Suitable porous binding substrates for reaction surfaces 22, 24 include the activated microporous membranes sold under the trademark IMMOBILON by the Millipore Corporation.

Reagent membrane 80 contains solubilizable analyte conjugate (30'). As discussed above, the analyte conjugate is preferably a conjugate of the analyte (32) with a ligand/marker (34) made up of, for example, a marker (e.g., a colored dye) and a ligand (e.g., biotin).

In use, the dipstick 44' including reaction chamber 20' is submerged in a test fluid containing an unknown amount of analyte. The chamber 20' is incubated for a short period of time, on the order of minutes or less, sufficient for test fluid to contact and pass sequentially through porous films 80, 22 and 24. Bibulous membrane 70 acts as a wick to drive this one-way flow. To release entrapped gas, the sidewalls 74 can be provided with one or more auxiliary openings 84, each screened with a hydrophobic but gas-permeable mesh. Analyte conjugate is solubilized as the test fluid passes through film 80. At the first reaction surface 22, competition between analyte and analyte conjugate for analyte-specific binding sites permits passage and contact with the second reaction surface 24 of analyte analog in proportion to the analyte concentration in the test fluid. The ligand/marker component of the analyte conjugate becomes bound to the ligand/marker-specific binding sites on the second reaction surface 24, producing a detectably marked surface indicative of analyte presence in the test fluid. Readout can be immediately achieved by, for eample, pulling tab 86 to rupture housing 72 and expose the second reaction surface 24 for visual or instrumental inspection.

Alternatively, as shown in FIG. 14, an aperture or transparent window 88 can be provided in dipstick 44' on the proximal side of the second reaction surface 24, for examination and detection of sequestered marker by absorption, reflected or emitted light. In such an embodiment, the second reaction surface 24 can take the form of a translucent and preferably transparent sheet of nitrocellulose or filter paper, avidinized on its distal surface. An opaque, and preferably white or otherwise reflective, porous membrane 90 may be disposed between the two reaction surfaces 22, 24 in order to shield any marker bound to the first surface 22 from view through window 88.

By providing predetermined quantities of the analyte conjugate and the analyte binding sites in porous films 80 and 22, respectively, and by providing chambers 20' of uniform fluid capacity, the concentration of analyte conjugate that binds to the second reaction surface 24 can be used to quantify the analyte concentration in the test fluid.

The dipstick 44' is typically provided with a plurality of chambers 20' having identical second reaction surfaces 24 but different analyte binding sites and analyte conjugates. Dipstick 44' can thus provide an immediate, one-step, multi-analyte readout, including suitable positive and negative controls.

Figure 15:
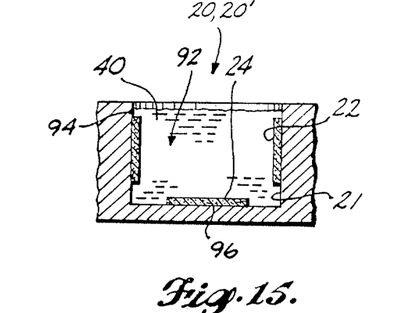
FIG. 15 is a section of a reaction chamber having the form of a modifed microtiter well.
Figure 16:
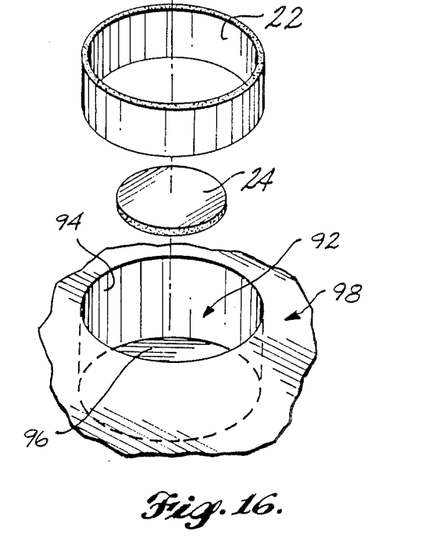
FIG. 16 is an exploded view of FIG. 15.

Referring now to FIGS. 15 and 16, a modified microtiter well 92 having a test fluid volume capacity of 100 to 200 μl can also serve as a reaction chamber 20, 20' of this invention. A first reaction surface 22 can be coaxially disposed on the sidewall 94 of the well 92, and a planar second reaction surface 24 can be disposed to cover all or part of the floor 96 of the well 92. In the displacement binding chamber 20, the analyte-binding sites (28) on the first reaction surface 22 are saturated with analyte conjugate (30). In the competitive binding chamber 20', the analyte conjugate 30 may be reversibly sequestered in solubilizable form on the sidewall 94 or floor 96 of the well, apart from the reaction surfaces 22, 24. Such reaction chambers 20, 20' can be conveniently filled with a test fluid sample 40 using an automatic pipette. Following an incubation period, any marker activity on the second reaction surface 24 can be conveniently read using, for example, an ELISA plate reader. A ring of containment wall 21 can be provided at the base of sidewall 94 so that substrate can be added to cover the second reaction surface 24 without contacting the first reaction surface 22. These embodiments 20, 20' are particularly well suited for repetitive laboratory testing by technical personnel using sophisticated instrumentation. For example, a plate 98 can be provided with a plurality of reaction chambers 20 and/or 20' for each test fluid to be assayed; some of the reaction chambers can be filled with replicate test fluid samples, and other reaction chambers can be filled with control solutions containing known concentrations of the analyte or analytes being assayed.

Figure 17:
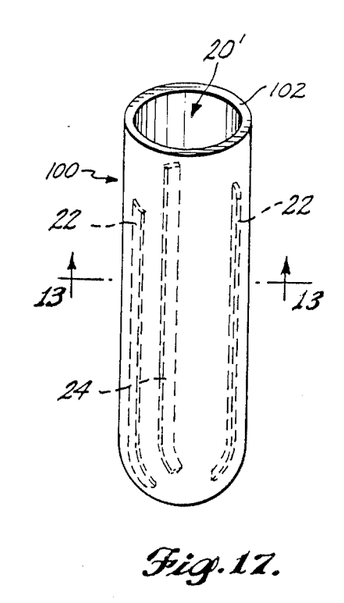
FIG. 17 is a plan view of a reaction chamber having the form of a modified test tube.
Figure 18:
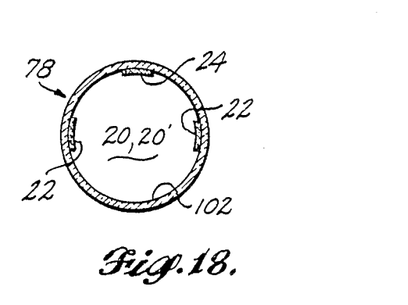
FIG. 18 is a section of FIG. 17.

Referring to FIGS. 17 and 18, in a related embodiment a modified test tube 100 can also serve as a reaction chamber 20, 20' of this invention. For example, first and second reaction surfaces 22, 24 can be disposed in nonoverlapping arrangement on the inner wall 102 of a test tube 100. In the displacement binding chamber 20, first reaction surface 22 is saturated with analyte conjugate 30; in the competitive binding chamber 20', analyte conjugate may be reversibly sequestered on the inner wall 102 apart from either reaction surfaces 22, 24. During the incubation period the test fluid sample (not shown) can be periodically stirred or vortexed in order to effect contacts between the reagents and the reaction surfaces 22, 24. If the first and second reaction surfaces

22, 24 are not diametrically opposed on the test tube wall 102, then colorimetric or fluorometric marker activity on second reaction surface 24 can be conveniently read by inserting tube 100 into a standard spectrophotometer or fluorometer.

The following Examples disclose representative analyte conjugates, suitable for use in either the displacement-binding or competitive-binding reaction chambers of this invention, and protocols for their preparation. These particular analyte conjugates employ bovine serum albumin (BSA) as a macromolecular carrier. To the BSA core are attached representative marker components (copper phthalocyanine dye molecules), ligand components (biotin), and analyte components (theophylline, in this instance). While BSA is here described as the carrier, any similarly functionalized species would suffice.

EXAMPLE 1

Marker component: selection and conjugation

Copper phthalocyanine (1) was selected as a potential marker component for the analyte conjugate due to its high molar absorptivity ($\lambda_{max}$ 678.5 nm, $\epsilon$=218,500 in chloronaphthalene). J. Chem. Soc., 2466, 1957. A modified version (2), rendered both water soluble by sulfonation and reactive by conversion to a dichlorotriazinylaminoethane sulfonamide, is readily available in crude form from several dye manufacturers (e.g., MX-G; Pro Chemical and Dye Inc., Somerset, Mass.).

(1)

(2)

In spite of the high molar absorptivity of the parent copper phthalocyanine compound (1), we found that the dichlorotriazinylethylene diamine sulfonamide derivative (2) ("CuPc") displayed an $\epsilon$ of 34,615 at $\lambda_{max}$ 666 nm in pH=8 phosphate buffer. Purification by column chromatography (silica, Dowex, cellulose Sephadex) or high performance liquid chromatography (HPLC) led to only a 15% increase in $\epsilon$, suggesting that factors other than impurities were responsible for the observed decrease in molar absorptivity ($\epsilon$). Related compounds are found to aggregate to form dimers and/or higher oligomers, with a dramatic decrease in $\epsilon$, when dissolved in aqueous solution at a variety of pH's and temperatures. Aust. J. Chem. 25:1661-1667, 1972. Since the bulk of such aggregates are dimers, they shall be referred to hereinafter as "dimers."

Compound (2) was linked to bovine serum albumin (BSA) under reaction conditions analogous to those described in J. Immunol. Meth. 13:305, 1976, for optimal binding of dichlorotriazinylaminofluorescein to IgG. To a stirred solution of BSA (25 mg, 3.6×10$^{-4}$ mmol) in pH=8 phosphate buffer (2.0 mL) was added compound (2) (100 mg, 3.6×10$^{-2}$ mmol). The mixture was stirred at 25° C. for 22 hours and then filtered through Sephadex G-25 with pH=8 phosphate buffer (10.0 mL). The filtrate was concentrated by Amicon ultrafiltration (50K; 600 mL pH=8 phosphate buffer, 600 mL distilled H$_2$O) and lyophilized to yield conjugate (3) (22 mg) as a blue solid with $\epsilon_{mol}$=400,000, assuming a MW=80,000 for conjugate (3).

$$\text{BSA—[CuPc)}_2\text{]}_{10} \qquad (3)$$

Related conjugates were prepared as shown in the following table:

| [BSA] | Eq (2)[+] | [(2)] | ml Buffer | Time | Eq (2)/BSA[*] | Solubility |
|---|---|---|---|---|---|---|
| 2.9 × 10$^{-5}$ | 103 | 3 × 10$^{-3}$ | 1.0 | 1 h | 0.8 | v |
| 3.6 × 10$^{-5}$ | 8 | 3 × 10$^{-4}$ | 10.0 | 22 h | 0.9 | v |
| 2.9 × 10$^{-5}$ | 34 | 1 × 10$^{-3}$ | 1.0 | 20 h | 5 | v |
| 1.8 × 10$^{-4}$ | 100 | 2 × 10$^{-2}$ | 10.0 | 22 h | 10 | v |
| 2.5 × 10$^{-4}$ | 497 | 1 × 10$^{-1}$ | 10.0 | 52 h | 19 | s |

[+]Equivalents of compound (2).
[*]Assumes (2) exists as a dimer.

Referring to the table, the number of dimers of compound (2) per BSA molecule, Eq(2)/BSA, was determined, after purification, using $\epsilon$=40,000 per dimer and assuming a molecular weight of 70,000. All the conjugates were highly water soluble (v), with the exception of the last entry (s) in the table. The binding of approximately 19 dimers substantially decreased the water solubility of the BSA carrier.

Ready visualization (A>0.1) of the dimer-linked BSA (based upon an $\epsilon$ if 40,000 per dimer unit, a biotin/avidin binding efficiency of 25%, and an avidin loading density of 100 μg/cm$^2$) conservatively requires the binding of at least 8 dimers of (2) per carrier. Such a sensitivity would allow the subject system, in both the displacement and competitive embodiments, to detect theophylline (01-100 ng/ml blood serum) but not analytes at concentrations in test fluid below on the order of 10 ng/ml, such as digoxin (0.5-2 ng/ml).

Aggregated copper phthalocyanine derivatives are reported to disaggregate in aqueous solutions containing urea and thiourea (Aust. J. Chem. 26:1545, 1973) or solvents such as acetone (Aust. J. Chem. 25:1661-1667, 1972). Our attempts to either disaggregate the bound dimer from conjugates like (3) or prepare the monomeric analog of (3) were unsuccessful in urea. However, conjugation of BSA to (2) in certain acetone:- buffer media led to the formation of predominantly monomeric copper phthalocyanine-linked BSA (4) with $\epsilon_{BSA}$ greater than $2 \times 10^6$.

BSA—(CuPc)₁₀               (4)

The order of addition as well as the ratio of acetone:-buffer proved to be very important in optimizing the coloring of the conjugates. Optimum pigmentation was achieved when the copper phthalocyanine derivative (2) was added to a solvent system composed of greater than 50 percent acetone in pH=8 phosphate buffer prior to the gradual addition of dry BSA.

A representative synthesis follows. BSA (75 mg, $1.1 \times 10^{-3}$ mmol) was added gradually to a stirred solution of compound (2) (109 mg, $1.1 \times 10^{-1}$ mmol) in a 70:30 mixture of acetone (87.0 mL) and pH=8 phosphate buffer (37.0 mL). The mixture was stirred at 25° C. for 48 hours, allowed to stand 24 hours, and then filtered through Sephadex G-25 with pH=8 phosphate buffer (30.0 mL). The filtrate was purified and concentrated by Amicon ultrafiltration (50K; 3.0 L pH=8 phosphate buffer, 2.0 L distilled H₂O), and lyophilized to yield conjugate (4) (17 mg) as a dark blue solid with $\epsilon_{mol}=2,100,000$, assuming a MW of 80,000 for (4).

Monomeric phthalocyanines can be similarly linked to other amine-bearing proteins, such as antibodies and antigens, to provide colored reagents useful for immunoassays generally. Aluminum phthalocyanine derivatives, in addition to being suitable chromogens, are advantageously luminescent as well.

EXAMPLE 2

Ligand component: biotinylation

Marker-labeled conjugates (3) and (4) were biotinylated with N-hydroxysuccinimidyl biotin (NHS-biotin) as described in the following representative protocol. To a stirred solution of conjugate (3) (5.0 mg. $6.3 \times 10^{-5}$ mmol) in pH=7 PBS (100 μl) was added NHS-biotin (0.4 mg, $1.3 \times 10^{-3}$ mmol) and a trace of ³N-NHS-biotin in dimethylformamide (DMF) (100 μl) and pH=7 PBS (20 || l). The mixture was stirred at 25° C. for two hours and then filtered through Sephadex G-25 with distilled H₂O (600 μl) to yield biotinylated conjugated (5) as a clear blue solution. The extent of radiolabel incorporation indicated that each molecule of (5) was biotinylated with an average of 10 biotin molecules.

(Biotin)₁₀-BSA-[(CuPc)₂]₁₀         (5)

Preliminary experiments conducted with such highly biotinylated conjugates of (3) and (4) revealed that neither species had any avidin binding efficiency. Using the procedure described above, we biotinylated conjugates (3) and (4) with a commercially available chain-extended biotin (sulfosuccinimidyl 6-biotinamidohexanate; Pierce Chemical Co., Rockford, Ill.) to produce the analogous biotinylated species bearing 15 and 12 biotins, respectively. These conjugated species were found to possess the requisite affinity for avidin.

EXAMPLE 3

Analyte component: tethered theophylline derivative

A tethered theophylline derivative was prepared for conjugation with protein, for use in an analyte conjugate to assay for theophylline in blood serum using the subject reaction chambers. First, theophylline acid (6) was prepared as described in Res. Comm. Chem. Path. Pharm. 13:497, 1976. A solution of 1.0 g (5.9 mmol) 5,6-diamino-1,3-dimethyluracil hydrate and 1.34 g (11.8 mmol) glutaric anhydride in 10.0 ml N, N-dimethylaniline was heated at 200° C. for three hours under nitrogen. After cooling to room temperature, the crystals thus formed were collected by filtration. The crystals were washed with benzene and recrystallized from water. Theophylline acid (6) was isolated as white granules, 700 mg (45%).

To a solution of 50 mg (0.188 mmol) acid (6), 4.0 ml pyridine, and 1.0 ml dioxane was added 43.2 mg (0.225 mmol) 1-ethyl-3-(3-dimethylaminopropyl) carbondiimide. The solution was stirred for one hour at room temperature. A solution of 35 mg (0.20 mmol) mono-t-butylcarbamate of 1,3-diamino-propane in 1.0 ml dioxane was added, and the resulting solution was stirred overnight. The reaction mixture was diluted with 10 ml methylene chloride, washed with dilute aqueous hydrochloric acid, dried over sodium sulfate and concentrated. Compound (7) was isolated as a white crystalline solid, 70 mg (88%).

To 50 mg (0.118 mmol) carbamate (7) was added 1.0 ml ice-cold trifluoroacetic acid/methylene chloride (1:3). The solution was stirred at 0° C. for one hour. Removal of solvent gave amine (8) as a clear, colorless oil, 36 mg (96%).

To a solution of 40.8 mg (0.118 mmol) succinimidyl 4-(N-maleimidomethyl) cyclohexane-1-carboxylate (SMCC) in 1.0 ml DMF was added 36 mg (0.112 mmol) amine (8) in 1.0 ml DMF. The resulting solution was stirred overnight at room temperature. The reaction mixture was diluted with 10 ml methylene chloride, washed with 3-10 ml portions water, and dried over magnesium sulfate. Removal of solvent gave maleimide (9) as a crystalline solid, 38 mg (63%).

(9)

Theophylline derivative (9) is suitable for conjugation to sulfhydryl bearing species such as the BSA derivatives prepared below. Sufficient length has been built into this tether to maximize the interaction of the theophylline (analyte) component with the antibody (analyte binding partner) on the first reaction surface. To assure the recognition of the theophylline-protein conjugate by the antibody, the immunogen should mimic the analyte complex, that is, the tether point to theophylline should be consistent for both purposes.

EXAMPLE 4

Incorporation of sulfhydryl groups into BSA

To a solution of 5.0 mg ($7.58 \times 10^{-5}$ mmol) BSA in 1.0 ml PBS (pH7) was added the desired number of equivalents of N-succimidyl 3-(2-pyridyldithio) propionate (SPDP) as a solution in absolute ethanol. After one hour at room temperature, the solution was filtered through Sephadex G-25.

To the resulting solution of the BSA/SPDP conjugate was added 1.2 mg ($7.58 \times 10^{-3}$ mmol) dithiothreitol (DTT). After 30 minutes at room temperature, the sulfhydryl (SH) content of the protein was assayed by measuring the absorbance of 2-thiopyridone at 343 nm. Representative results are shown below.

| Eq. SPDP | SH/BSA |
|---|---|
| 5 | 4 |
| 10 | 6 |
| 25 | 13 |
| 50 | 28 |

EXAMPLE 5

Conjugation of analyte component to BSA

The above BSA/SPDP conjugates bearing free sulfhydryl groups were reacted with theophylline analog (9) as follows. To a solution of 30 mg ($4.55 \times 10^{-4}$ mmol) BSA/SPDP conjugate (SH/BSA determined to be 3) was added 30 equivalents ($1.37 \times 10^{-2}$ mmol) theophylline maleimide (9). After stirring overnight at room temperature, the reaction mixture was filtered through Sephadex G-25 and dialyzed against distilled water. Lyophilization gave 25 mg of a BSA/theophylline conjugate. Determination of 3 theophylline haptens per BSA was made by absorbance measurement at $\lambda 280$ nm.

EXAMPLE 6

Construction of the analyte conjugate

In the analyte conjugate, the marker, ligand, and analyte components may be bound directly to a single carrier molecule. The resulting complex (10), shown schematically below, is preferably formed by covalently binding monomeric phthalocyanines to BSA, followed by biotinylation of the BSA and conjugation of theophyllines to the BSA, all as described above.

(10)

Two embodiments of the analyte conjugate which employ pairs of carrier molecules are shown below.

(11)

(12)

The preparation of these analyte conjugates follows the protocols described above; namely, dye binding, biotinylation, and theophylline conjugation to BSA. Formation of analyte conjugate (11) involves the linking of a BSA bearing phthalocyanine components to a BSA bearing biotins and theophyllines. Similarly, conjugate (12) is formed by linking a biotinylated, dye-labelled BSA to a BSA to which theophyllines have been conjugated. The BSA—BSA link is accomplished by introduction of sulfhydryl groups into one of the BSA components, as described above, and the incorporation of functionalities reactive toward sulfhydryls, such as α- iodoacetates or maleimides, into the BSA of the complement.

An extension of this methodology results in the modular analyte conjugate (13) represented schematically below.

The preparation of the individual BSA conjugates and the assembly of the BSA links are as described above.

EXAMPLE 7

Avidinized analyte conjugate

In a complementary embodiment of the disclosed immunoassay, the analyte conjugate may contain an avidin ligand component, while the second reaction surface is biotinylated. Two representative avidinized analyte conjugates are shown schematically below.

Preparation of (14) and (15) follows from the chemistries described above. For (14), a dye-BSA conjugate is covalently linked to an avidin-theophylline conjugate in a manner analogous to the linking of BSA conjugates described above. The formation of (15) involves the linking of avidin to a BSA bearing both dye and theophylline.

EXAMPLE 8

BSA protected dye-BSA conjugate

The hydrophobicity of the phthalocyanine components of the above analyte conjugates may lead to non-specific binding of the conjugates to some surfaces. This problem is solved by blanketing the dye-BSA complexes with additional BSA.

The BSA protected version (16) of the dye-BSA conjugate utilizes the chemistries described above for linking BSA conjugates and BSA-avidin conjugates. Specifically, the dye-BSA complex is treated with SMCC to yield a dye-BSA conjugate bearing maleimide groups. To this complex is added an excess of BSA molecules which have been enriched with sulfhydryl groups. Reaction of the BSA sulfhydryl groups with the maleimide functions of the dye-BSA conjugates results in the covalent binding of the two species to produce BSA protected dye-BSA conjugates such as (16), to which ligands such as biotin and analyte components such as (9) are then bound.

Conjugate (16) can also be used to diminish oxygen quenching of luminescence, e.g., where metalloporphyrins are used as the marker component, by sequestering the marker ("dye") in a relatively protective environment. For example, by shielding oxygen-quenchable luminescent markers such as platinum porphyrins within the hydrophobic core of proteinaceous conjugate (16), oxygen is physically excluded from interacting with the metal in its excited state. Quenching of the luminescent signal by vibrational deactivation, such as is known to occur in lanthanide porphyrins, is similarly reduced by sequestering, e.g., a ytterbium porphyrin in a protective conjugate such as (16).

While the present invention has been described in conjunction with a preferred embodiment and illustrative examples, one of ordinary skill after reading the foregoing specification will be able to effect various changes, substitutions of equivalents, and other alterations to the subject matter set forth herein. It is therefore intended that the protection granted by Letters Patent hereon be limited only by the definition contained in the appended claims and equivalents thereof.

The embodiments of the invention in which an exclusive property or privilege is claimed are defined as follows:

1. A device for detecting an analyte in a test fluid, comprising a reaction chamber having reagent, reaction, and detection surfaces wherein at least the detection surface does not overlap either the reagent surface or the reaction surface, the reaction chamber being adapted to receive and retain a predetermined volume of the test fluid in fluid communication with said reagent, reaction, and detection surfaces, the reagent surface having an analyte conjugate reversibly bound thereto, the analyte conjugate comprising a ligand/marker conjugated to an analyte component, the reaction surface having an analyte binding partner immobilized thereon, and the detection surface having a ligand/marker binding partner immobilized thereon.

2. The device of claim 1 wherein the analyte binding partner comprises an antibody, antigen, or hapten.

3. The device of claim 1 wherein the ligand/marker binding partner comprises avidin or biotin.

4. The device of claim 1 wherein the analyte binding partner and the ligand/marker binding partner comprise different antibodies.

5. The device of claim 1 wherein the reaction chamber is adapted to receive and direct the test fluid sequentially past the reagent, reaction, and detection surfaces.

6. The device of claim 5 wherein at least one of said reagent and reaction surfaces comprises a microporous membrane.

7. The device of claim 5 wherein the predetermined test fluid volume capacity of the reaction chamber is on the order of 10 to 100 μl.

8. The device of claim 5 wherein the reaction chamber further comprises wick means disposed downstream of the detection surface.

9. The device of claim 8 wherein the reaction chamber further comprises valve means for releasing from the reaction chamber air displaced by the received volume of test fluid.

10. The device of claim 5 wherein the reaction chamber is detachably mounted on an insoluble support.

11. The device of claim 5 wherein the detection surface is affixed to an insoluble support.

12. The device of claim 11 wherein the insoluble support comprises an aperture or window exposing the detection surface to visual or instrumental inspection.

13. The device of claim 5 wherein a plurality of said reaction chambers are detachably mounted on an insoluble support, the reaction chambers having identical ligand/marker binding partners but different analyte binding partners.

14. The device of claim 1 wherein the predetermined test fluid volume capacity of the reaction chamber is on the order of 100 to 200 μl.

15. The device of claim 14 wherein said reaction chamber comprises a microtiter well.

16. The device of claim 1 wherein said reaction chamber comprises a test tube.

17. The device of claim 1 wherein said analyte conjugate comprises a metallophthalocyanine selected from copper, silicon, and aluminum phthalocyanines.

18. The device of claim 17 wherein said phthalocyanine is in a monomeric form.

19. The device of claim 1 wherein said analyte conjugate comprises a luminescent metalloporphyrin derivative.

20. The device of claim 19 wherein said luminescent metalloporphyrin derivative is selected from ytterbium and platinum porphyrins.

21. A method of detecting an analyte in a test fluid, comprising the steps of:
providing a reaction chamber having reagent, reaction, and detection surfaces wherein at least the detection surface does not overlap either the reagent surface or the reaction surface, the reaction chamber being adapted to receive and retain a predetermined volume of the test fluid in fluid communication with said reagent, reaction, and detection surfaces, the reagent surface having an analyte conjugate reversibly bound thereto, the analyte conjugate comprising a ligand/marker conjugated to an analyte component, the reaction surface having an analyte binding partner immobilized thereon, and the detection surface having a ligand/marker binding partner immobilized thereon;
introducing a volume of test fluid suspected of containing analyte into the reaction chamber in fluid communication with the reagent, reaction, and detection surfaces;
retaining the volume of test fluid in the reaction chamber to permit solubilization of analyte conjugate from the reagent surface, binding of analyte and solubilized analyte conjugate to analyte binding partner on the reaction surface, and binding of solubilized analyte conjugate to ligand/marker binding partner on the detection surface; and,
thereafter measuring the activity of sequestered ligand/marker on the detection surface, the measured activity being a function of the analyte concentration that is referable to standards and controls.

22. The method of claim 21 wherein the reaction chamber is adapted to receive and direct the test fluid sequentially past the reagent, reaction, and detection surfaces.

23. The method of claim 21 wherein the reaction chamber comprises a microtiter well.

24. A test kit comprising the device of claim 1 in combination with comparative test results that associate ligand/marker activity on the detection surface with specific concentrations of analyte in test fluid.

25. The test kit of claim 24 wherein the comparative test results comprise a color chart.

26. A test kit comprising the device of claim 5 in combination with comparative test results that associate ligand/marker activity on the detection surface with specific concentrations of analyte in test fluid.

27. A device for detecting an analyte in a test fluid, comprising a microtiter well having nonoverlapping reagent, reaction, and detection surfaces, the microtiter well being adapted to receive and retain a predetermined volume of the test fluid in fluid communication with said reagent, reaction, and detection surfaces, the reagent surface having an analyte conjugate reversibly bound thereto, the analyte conjugate comprising a ligand/marker conjugated to an analyte component, the reaction surface having an analyte binding partner immobilized thereon, and the detection surface having a ligand/marker binding partner immobilized thereon.

28. The device of claim 27, wherein the predetermined test fluid volume capacity of the microtiter well is on the order of 100 to 200 μl.

29. A method of detecting an analyte in a test fluid, comprising the steps of:
providing at least one microtiter well having nonoverlapping reagent, reaction, and detection surfaces, the microtiter well being adapted to receive and retain a predetermined volume of test fluid in fluid communication with said reagent, reaction, and detection surfaces, the reagent surface having an analyte conjugate reversibly bound thereto, the analyte conjugate comprising a ligand/marker conjugated to an analyte component, the reaction surface having an analyte binding partner immobilized thereon, and the detection surface having a ligand/marker binding partner immobilized thereon;
introducing a volume of test fluid suspected of containing analyte into the reaction chamber in fluid communication with the reagent, reaction, and detection surfaces;
retaining the volume of test fluid in the reaction chamber to permit solubilization of analyte conjugate from the reagent surface, binding of analyte and solubilized analyte conjugate to analyte binding partner on the reaction surface, and binding of solubilized analyte conjugate to ligand/marker binding partner on the detection surface; and,
thereafter measuring the activity of sequestered ligand/marker on the detection surface, the measured activity being a function of the analyte concentration that is referable to standards and controls.

30. The method of claim 29, wherein the predetermined test fluid volume capacity of the microtiter well is on the order of 100 to 200 μl.

* * * * *

UNITED STATES PATENT AND TRADEMARK OFFICE
CERTIFICATE OF CORRECTION

PATENT NO. : 4,803,170

DATED : February 7, 1989

INVENTOR(S) : Stanton et al.

Page 1 of 2

It is certified that error appears in the above-identified patent and that said Letters Patent is hereby corrected as shown below:

[57] ABSRACT, line 15, "first" should be --first,--.

[57] ABSTRACT, lines 16 and 17, "completes" should be --competes--.

Column 9, line 62, "HPR" should be --HPO--.

Column 10, line 25, "HPR" should be --HPO--.

Column 14, line 58, "(01-100" should be --(10-100--.

Column 15, line 40, "$^3$N-NHS-biotin" should be --$^3$H-NHS-biotin--.

Column 15, line 41, "(20 ∥ 1)" should be --(20 μl)--.

Column 15, line 43, "distilled $H_2O$" should be --phosphate buffered saline--.

Column 16, line 60, "(N-maleimidomethyl) cyclohexane" should be --(N-maleimidomethyl)cyclohexane"--

Column 17, line 28, "complex," should be --complex;--.

Column 18, line 53, in schematic diagram (12), "theophyllin" should be --theophylline--.

Column 19, line 25, in schematic diagram (14), "theophyllin" should be --theophylline--.

UNITED STATES PATENT AND TRADEMARK OFFICE
CERTIFICATE OF CORRECTION

PATENT NO. : 4,803,170
DATED : February 7, 1989
INVENTOR(S) : Stanton et al.

It is certified that error appears in the above-identified patent and that said Letters Patent is hereby corrected as shown below:

Column 19, lines 51-68, in schematic diagram (16), all lines extending to "dye" should be shorter than the lines extending to "BSA":

Signed and Sealed this

Thirty-first Day of October, 1989

*Attest:*

DONALD J. QUIGG

*Attesting Officer*  *Commissioner of Patents and Trademarks*